United States Patent [19]

Yoshida et al.

[11] Patent Number: 5,045,458
[45] Date of Patent: Sep. 3, 1991

[54] ANTIBIOTICS PB-6042S

[75] Inventors: Tadashi Yoshida, Toyono; Teruo Hattori, Takarazuka; Koichi Matsumoto; Yoshihiro Terui, both of Toyonaka; Junichi Shoji, Hirakata, all of Japan

[73] Assignee: Shionogi & Co., Ltd., Osaka, Japan

[21] Appl. No.: 424,366

[22] Filed: Oct. 19, 1989

[30] Foreign Application Priority Data

Oct. 20, 1988 [JP] Japan ................... 63-266575

[51] Int. Cl.$^5$ .................. A61K 31/365; C12P 17/04; C07D 307/60; C12R 1/01
[52] U.S. Cl. ..................... 435/126; 549/318; 435/822
[58] Field of Search ................ 435/126, 822; 549/318

[56] References Cited

FOREIGN PATENT DOCUMENTS

| | | | |
|---|---|---|---|
| 0332216 | 9/1989 | European Pat. Off. | 435/126 |
| 0365329 | 4/1990 | European Pat. Off. | 435/126 |
| 3813806 | 11/1989 | Fed. Rep. of Germany | 435/126 |
| 0258173 | 12/1985 | Japan | 435/126 |
| 3096182 | 4/1988 | Japan | 435/126 |
| 1071867 | 3/1989 | Japan | 435/126 |

OTHER PUBLICATIONS

Keller-Juslen, "J. Antibiotics", 35(2), 142-150.

*Primary Examiner*—Herbert J. Lilling
*Attorney, Agent, or Firm*—Wenderoth, Lind & Ponack

[57] ABSTRACT

A compound of the formula (I):

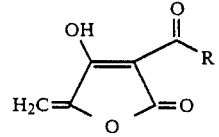

wherein R is:
$(CH_2)_8CH_3$,
$(CH_2)_3CH(cis)CH(CH_2)_5CH_3$,
$(CH_2)_{10}CH_3$, or
$(CH_2)_4CH(cis)CH(CH_2)_6CH_3$.

or salt thereof, and a microorganism producing the compound are provided.

4 Claims, 3 Drawing Sheets

FIG. 3D

ANTIBIOTICS PB-6042S

Currently, a large variety of useful antibiotics are available, but only a few of them including lustomycin exhibit antibacterial activity exclusively against anaerobic bacteria. Therefore, there is continuing need for antibiotics having more specific and greater antibacterial activity against anaerobic bacteria.

Under such circumstances, this invention provides new antibiotics PB-6042A, PB-6042B, PB-6042C, and PB-6042D or salts thereof, a new strain producing the above antibiotics, and a method of producing them.

The antibiotics PB-6042A, B, C, and D, which may be referred to as PB-6042s as a whole, are products of a new strain designated *Enterobacter agglomerance* PB-6042. They are acidic compounds and are specific against anaerobic bacteria and exhibit higher antibacterial activity than the known antibiotics such as lustomycin having similar antibacterial spectrum.

Since the compounds of the invention exhibit antibiotic activity exclusively against anaerobic bacteria, it will be understood that the use of the compounds are advantageous for the treatment of infectious diseases such as clitis caused by anaerobic enterobacteria. Additionally, it is expected that the compounds of the invention exhibit any additional physiological activity which is therapeutically useful, for example, platelet aggregation-inhibiting activity, anti-tumor activity and so on, because the compounds have very unique chemical structure as stated below.

The present invention includes the salts of the compounds of the invention, particularly pharmaceutically acceptable salts such as sodium salts.

In the accompanying drawings.

The compounds of the invention have a unique chemical structure, which has not been found in known antibiotics. Detailed discussion on physicochemical properties and chemical structures of the compounds of the invention are provided below.

PHYSICOCHEMICAL PROPERTIES

Antibiotics PB-6042A, B, C, and D have all been found to be acidic substances by filter paper electrophoresis and bioautography. Other physicochemical properties of PB-6042s in the form of sodium salt are listed below.

Color: PB-6042s are all colorless crystalline powder.

Solubility: PB-6042s are all soluble in DMSO, methanol, ethanol, and ethyl acetate, are slightly soluble in chloroform, and are insoluble in water, ether, and petroleum ether.

Stability: PB-6042s are all unstable in an acidic solvent. Immediately after the free compound is evaporated to dryness and allowed to stand, it spontaneously polymerizes to produce an insoluble polymer.

Figure 1A:
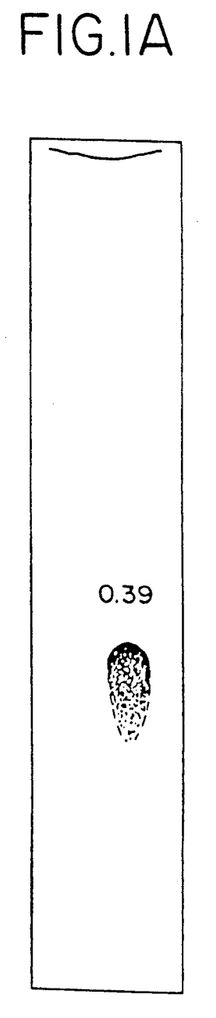
FIG. 1 shows TLC chromatography of PB-6042s.
Figure 1B:
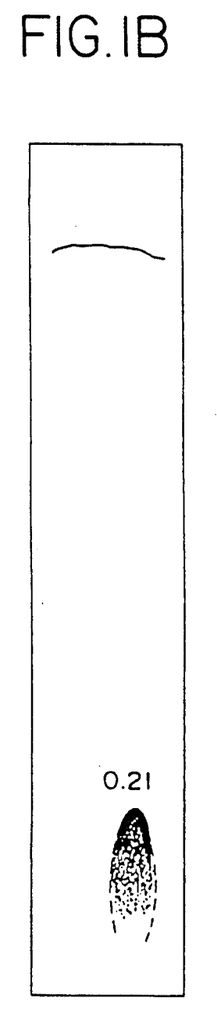

TLC: A solution containing a mixture of PB-6042A, B, C, and D was spotted on Merck silica gel GF plate, and developed in chloroform/methanol (9:1) [developing solvent A], and in butyl acetate/methanol (9:1) [developing solvent B]. The resultant TLC chromatograms are shown in FIG. 1 of the accompanying drawings. As shown in FIG. 1, Rf values of all the compounds were the same, and approximately 0.21 and 0.39 in the developing solvents A and B, respectively.

Figure 2:
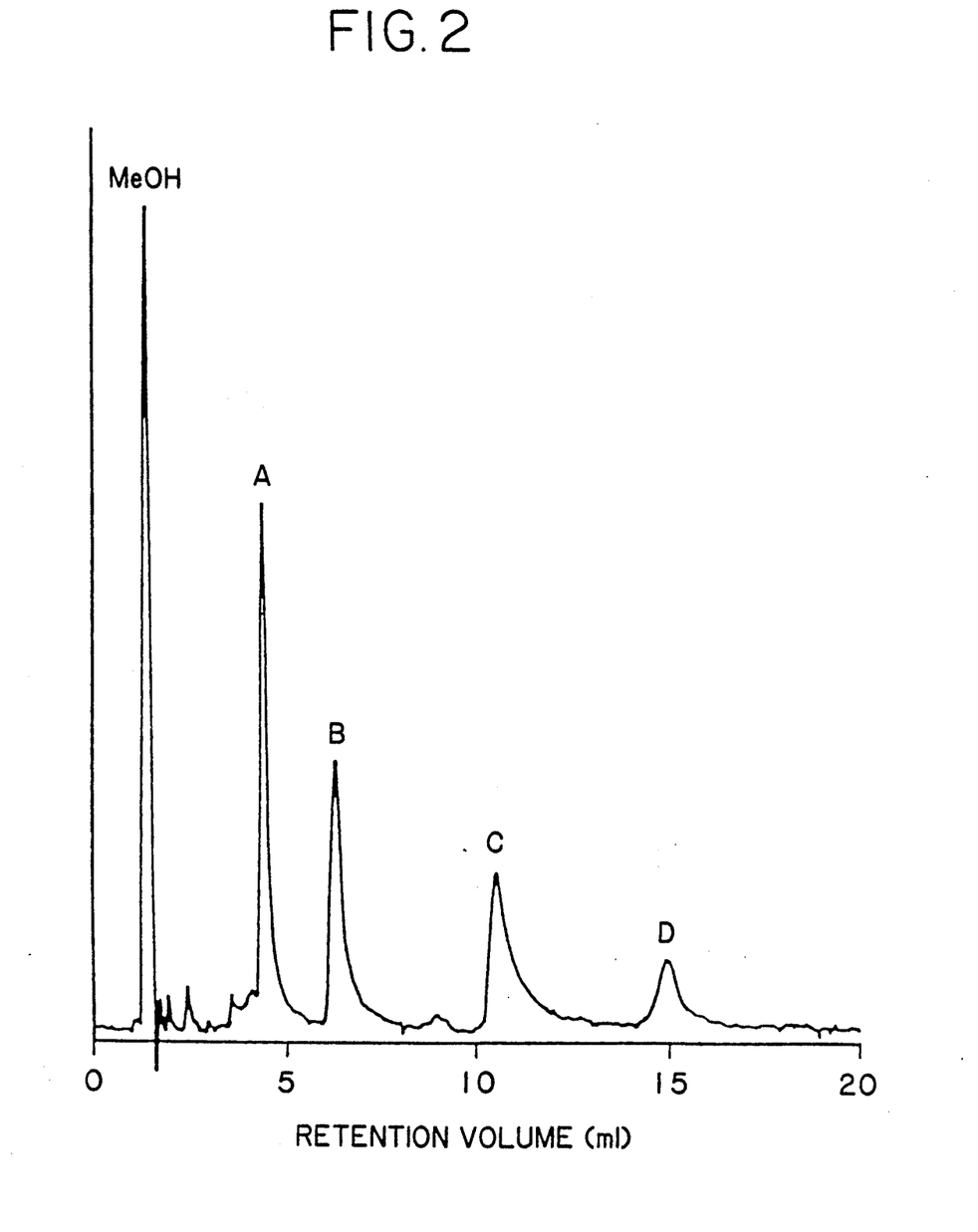
FIG. 2 shows HPLC chromatography of PB-6042s.
Figure 3A:
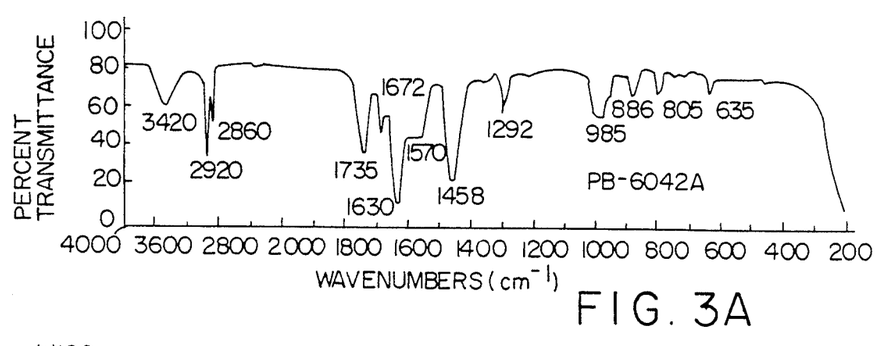
FIG. 3 shows IR spectra of PB-6042s.
Figure 3B:
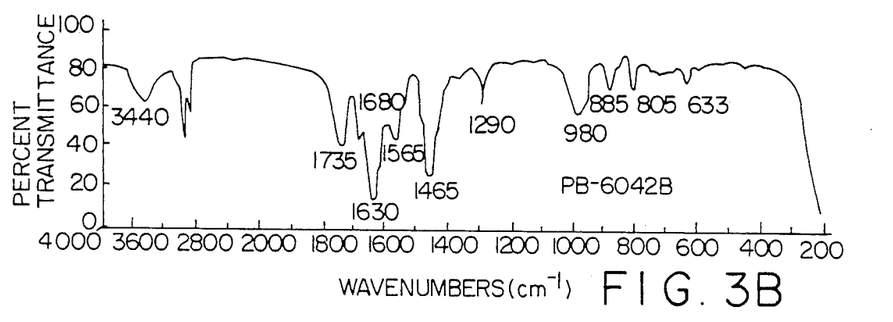
Figure 3C:
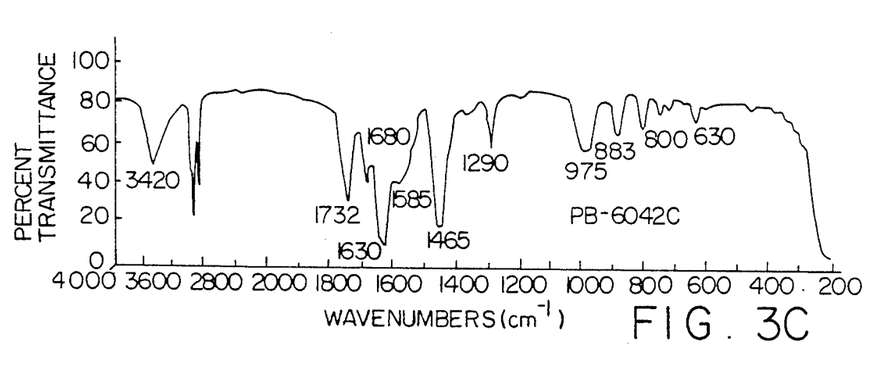
Figure 3D:
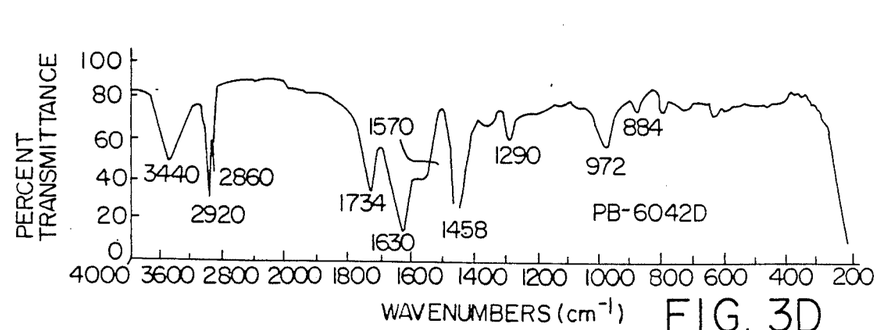

HPLC: The mixture of PB-6042s was subjected to high performance liquid chromatography (HPLC) under the following conditions.
Column: Nucleocil 5 $C_{18}$ (No.3), 4.6×250mm,
Eluent: 40% acetonitrile/50mM PBS, pH =7.5 (50mM $Na_2SO_4$),
Flow rate: 1 ml/min.,
OD: 254 nm,
Chart speed: 0.5 cm/min.
FIG. 2 shows that PB-6042s are separated from each other under the above conditions.

MELTING POINT, ELEMENTAL ANALYSIS, AND SECONDARY ION MASS SPECTRUM
(SI-MS) Melting point, Elemental analysis, and Secondary Ion Mass Spectrum (SI-MS):

PB-6042A

Melting point; 113–115° C.
Elemental analysis; Found C; 61.50, H; 7.36, Na; 7.47. Calcd. for $C_{15}H_{21}O_4Na(288)$, C; 62.50, H;7.29, Na; 7.47.
Calcd. for $C_{15}H_{21}O_4Na.1/4H_2O$, C; 61.53, H;7.35, Na; 7.86
SI-MS(m/z); 311(M+Na)

PB-6042B

Melting point; 85°–88° C.
Elemental analysis; Found C; 63.99, H; 7.51, Na; 6.91. Calcd. for $C_{17}H_{23}O_4Na(314)$, C; 64.96, H;7.32, Na; 7.32.
Calcd. for $C_{17}H_{23}O_4Na.1/4H_2O$, C; 64.05, H;7.37, Na; 7.22.
SI-MS(m/z); 337(M+Na)

PB-6042C

Melting point; 125°–128° C.
Elemental analysis; Found C; 63.90, H; 8.16, Na; 6.75 Calcd. for $C_{17}H_{25}O_4Na(316)$, C; 64.55, H;7.91, Na; 7.27.
Calcd. for $C_{17}H_{25}O_4Na.1/4H_2O$, C; 63.65, H;7.80, Na; 7.17.
SI-MS(m/z); 339(M+Na)

PB-6042D

Melting point; 103°–106° C. Elemental analysis; Found C; 65.56, H; 8.07, Na; 6.11. Calcd. for $C_{19}H_{27}O_4Na(342)$, C; 66.66, H;7.89, Na; 6.72. Calcd. for $C_{19}H_{27}O_4Na.1/4H_2O$, C; 65.80, H;7.80, Na; 6.63.
SI-MS(m/z); 365(M+Na)

UV spectrum: PB-6042A, B, C, and D show absorption maximum at the same wavelength in UV spectra ($\lambda_{max}$), and they also have the same values of the extinction coefficients ($\epsilon$). The common absorption maxima, $\lambda_{max}$ ($\lambda$), in different solvents are shown below:
$\lambda_{max}(\lambda)$ = 248 nm (18777), 298 nm (9216) in methanol,
$\lambda_{max}(\lambda)$ = 248nm, 298 nm in dil NaOH/methanol,
$\lambda_{max}(\lambda)$ = 215 nm (7640), 285 nm (12239) in dil HCl/methanol Blue shift was observed in acidic conditions.

IR spectrum (KBr): FIG. 3 shows IR spectra of PB-6042A, B, C, and D, which are very similar to each other.

Circular dichroism (CD): The CD for each of PB-6042s in 220–320 nm was zero in methanol. This shows that none of PB-6042s possesses optical activity. It is concluded from the afore physicochemical characteristics that antibiotics PB-6042A, B, C, and D have very similar structures and that their chromophores are quite identical.

DISCUSSION ABOUT STRUCTURE Discussion about structure

[1]. PB-6042A

$^1$H and $^{13}$C NMR spectra of PB-6042A sodium salt in CDCl$_3$-CD$_3$OD (15:1) and those in DMSO-d$_6$ demonstrated the presence of an alkyl group and an exo-methylene group, as well as five quarternary carbons. IR spectrum indicated the presence of unsaturated lacton (1735 cm$^{-1}$) and conjugated unsaturated ketone (1670, 1630 cm$^{-1}$), while it showed the absence of a carboxylic group in spite of the fact that PB-6042A is an acidic substance according to the paper electophoresis and bioautogram analysis. It is believed that PB-6042A has a structure inducing the tautomerism shown below, in the light of the fact that the degree of unsaturation of the compound is estimated to be 5 judging from its molecular formula and the fact that the signals of an exo-methylene carbon, five quaternary carbons and an alkyl methylene carbon adjacent to the chromophore are all very broad in $^{13}$C-NMR spectrum:

wherein R is (CH$_2$)$_8$CH$_3$.

The broadening is attributed to chemical shift exchange due to the tautomerism. The resonance structure shown above stabilized the anionic form and contributes to the acidic property of PB-6042s.

PB-6042A was reduced with H$_2$/PtO$_2$ in order to convert the exo-methylene group to a methyl group (See Reference Example 1), and the resultant product was analyzed by UV spectroscopy, revealing that λ$_{max}$ was 230 and 265 in methanol, 230 and 263 in dil NaOH/methanol, and 204 and 269 in dil HCl/methanol. The reduced product maintained antibacterial activity and acidic property. $^{13}$C signals of the resultant chromophore also exhibited the broadening in CDCl$_3$-CD$_3$OD (15:1) at 24° C. In DMSO-d$_6$ at 24° C., $^{13}$C signals assignable to three tautomers were observed. At high temperature, the signals of the tautomers coalesced. The resonance structure shown below also contributes to the acidic property.

reduced form of PB-6042A wherein R is (CH$_2$)$_8$CH$_3$.

The reduced product was then methylated by a conventional procedure (Reference Example 2) and the resultant compound was analyzed by $^{13}$C-NMR spectra, in which no broad signals were found. Long-range C-H shift correlation spectroscopy was employed for the assignment of the quaternary carbons and revealed that the methylated product has the following structure:

Therefore, PB-6042A is believed to have the following structure:

[2]. PB-6042B, C, and D

The structures of PB-6042B, C, and D were determined by comparing their NMR spectra with that of PB-6042A whose structure had been determined in the above. $^1$H and $^{13}$C NMR data of PB-6042s are shown in Tables 1 and 2.

Structures of PB-6042s common basal structure side chain: R

TABLE 1

| proton No. | A | B | C | D |
|---|---|---|---|---|
| 1 a | 5.12 (br-s) | 5.14 (br-s) | 5.14 (br-s) | 5.12 (br-s) |
| 1 b | 4.73 (br-s) | 4.82 (br-s) | 4.82 (br-s) | 4.79 (br-s) |
| 1' | 2.75 (t,7) | 2.82 (t,7) | 2.81 (m) | 2.82 (m) |
| 2' | 1.51 (m) | 1.62 (m) | 1.57 (m) | 1.57 (m) |
| 3' | 1.2~1.35 (m) | 2.10 (m) | 1.2~1.4 (m) | 1.2~1.4 (m) |
| 4' | 1.2~1.35 (m) | ~5.37 (m) | 1.2~1.4 (m) | ~2.01 (m) |
| 5' | 1.2~1.35 (m) | ~5.37 (m) | 1.2~1.4 (m) | ~5.34 (m) |
| 6' | 1.2~1.35 (m) | 2.01 (m) | 1.2~1.4 (m) | ~5.34 (m) |
| 7' | 1.2~1.35 (m) | 1.2~1.4 (m) | 1.2~1.4 (m) | ~2.01 (m) |
| 8' | 1.2~1.35 (m) | 1.2~1.4 (m) | 1.2~1.4 (m) | 1.2~1.4 (m) |
| 9' | 0.87 (t) | 1.2~1.4 (m) | 1.2~1.4 (m) | 1.2~1.4 (m) |
| 10' | — | 1.2~1.4 (m) | 1.2~1.4 (m) | 1.2~1.4 (m) |
| 11' | — | 0.88 (t,7) | 0.88 (t,7) | 1.2~1.4 (m) |
| 12' | — | — | — | 1.2~1.4 (m) |
| 13' | — | — | — | 0.88 (t,6.8) |

$^1$H NMR data on PB-6042s (CDCl$_3$—CD$_3$OD (15:1), 24° C.)

TABLE 2

$^{13}$C NMR data on PB-6042s (CDCl$_3$—CD$_3$OD (15:1), 24° C.)

| carbon No. | A | B | C | D |
|---|---|---|---|---|
| 1 | 90.0t | 89.9t | 89.8t | 89.7t |
| 2 | 153.3s | 153.4s | 153.5s | 153.6s |
| 3 | 182.4s | 182.5s | 182.4s | 182.4s |
| 4 | 97.1s | 97.1s | 97.1s | 97.0s |
| 5 | 173.3s | 173.3s | 173.3s | 173.2s |
| 6 | 199.3s | 199.0s | 199.3s | 199.1s |
| 1' | 40.7t | 40.3t | 40.8t | 40.7t |
| 2' | 25.2t | 25.3t | 25.3t | 25.4t |
| 3' | 29.7t$^a$ | 27.2t$^a$ | 29.8t$^a$ | 29.8t$^a$ |
| 4' | 29.7t | 129.1d$^b$ | 29.8t | 27.3t |
| 5' | 29.7t | 130.6d$^b$ | 29.8t | 129.8d$^b$ |
| 6' | 29.4t$^a$ | 27.3t$^a$ | 29.8t | 130.1d$^b$ |
| 7' | 32.1t | 29.1t$^c$ | 29.8t | 27.3t |
| 8' | 22.7t | 29.8t$^c$ | 29.4t$^a$ | 29.1t |
| 9' | 14.1q | 31.9t | 32.0t | 29.8t |
| 10' | — | 22.7t | 22.7t | 29.5t$^a$ |
| 11' | — | 14.1q | 14.1q | 31.9t |
| 12' | — | — | — | 22.7t |
| 13' | — | — | — | 14.1q |

Note:$^{a,b,c}$: Two numerical data bearing the same superscripts is replaceable each other in each compound.

On the basis of the data listed above, it has been determined that PB-6042A, B, C, and D have the common basal structure and differ from each other only in the side chain structures.

The exact structure of the side chain of PB-6042B was determined by using $^1$H-NMR decoupling method. The decoupling method allowed to correlate δ values, 2.82, 1.62, 2.10, 5.37 (two occurrences), and 2.01 in this order. The tip structure of the side chain following an unsaturated bond was determined by integral analysis of $^1$H-NMR, $^{13}$C-NMR and mass spectra. These results led to the determination of the structure of PB-6042B as shown in the formula (II) hereinafter.

$^1$H-NMR spectrum of the PB-6042C was similar to that of PB-6042A, except that the integral strength at 1.2–1.4 (m) was 4/3 times stronger than that of PB-6042A. In addition, $^{13}$C-NMR showed that PB-6042C possessed additional two CH$_2$(t) as compared with PB-6042A. Therefore, the structure of PB-6042C was determined to have the structure shown in the formula (III) hereinafter. Mass spectrum confirmed this.

Finally, as for the structure of PB-6042D, the exact position of an unsaturated bond could not be determined by NMR, because the δ values of two CH$_2$ locating adjacent to the unsaturated bond are fallen within the δ values, approximately 2.01. However, the exact position of the unsaturated bond was determined by oxidative cleavage of unsaturated bond and analyzing the resultant saturated fatty acid.

The unsaturated bonds in the side chains of PB-6024B and D were determined as cis-form because δ value of methylene carbon adjacent to the unsaturated bond was approximately 27 in both PB-6042C and D which value corresponds to that of the cis-form of the following known compounds.

Based on the foregoing studies, the structures of PB-6042s are determined as follows:

wherein R is:
 (CH$_2$)$_8$CH$_3$,
 (CH$_2$)$_3$CH(cis)CH(CH$_2$)$_5$CH$_3$,
 (CH$_2$)$_{10}$CH$_3$, or
 (CH$_2$)$_4$CH(cis)CH(CH$_2$)$_6$CH$_3$.

Furthermore, each compound of PB-6042s is as follows:

antibiotic PB-6042A of the formula (I):

-continued antibiotic PB-6042B of the formula (II):

antibiotic PB-6042C of the formula (III):

and antibiotic PB-6042D of the formula (IV):

Production of PB-6042s

Antibiotics PB-6042A, B, C, and D are produced by culturing *Enterobacter agglomerans* PB-6042. The antibiotics can be recovered using various isolation and purification procedures which are known in the art.

*Enterobacter agglomerans* was isolated from a water sample from a river locating at Kita-ku, Kobe-shi in Japan. For convenience in describing the strain, *Enterobacter agglomerans* PB-6042, it is referred to as PB-6042 hereinafter. PB-6042 was deposited at Fermentation Research Institute, Higashi 1-1-3, Thukuba-shi, Ibaraki-ken, Japan, under Budapest Treaty with the accession number FERM BP-2549 (Date: Aug. 6, 1988).

Characteristics of PB-6042

1. G+C mol %: 53.0 (determined by HPLC)
2. Morphological Characteristics

PB-6042 was grown on a agar slant containing meat extract for 24 hours at 28° C., and the following characteristics were observed.

The strain is a Gram-negative and straight rod of $0.5-0.7(\mu) \times 2-5(\mu)$ in size. It has 3 to 5 peritrichous flagella and shows active motility in the meat extract broth described hereinafter.

3 Cultural Characteristics i) Meat extract agar plate (at 28° C., for 3 days)

Most of the colonies showed round shape of translucent grayish pale brown color. The colonies had entire margin, smooth and glistening surface. The elevation of colonies was flat to slightly convex. A few of the colonies showed whitish and slightly opaque color, although other characteristics were the same as the translucent colonies.

That is to say, any difference between both colonies was not found in the cell morphology, in the Gram stain, and in physiological properties, described hereinafter. However, slight difference was observed in motility of both colonies. Thus, in stab culture of the semisolid agar medium, the major translucent colony grew evenly to form uniform turbidity throughout the tube, which showed active motility, while the minor opaque colony grew only around the stab line, which showed poor motility. Such difference in motility identified the minor colony as a variant of the major colony. Generation of gas and production of soluble pigments were not observed in both colonies.

ii) Meat extract broth (at 28° C., for 2-11 days)

PB-6042 grew forming uniform turbidity, and produced pale yellow sediment. Thin and flaky pellicle, which was grayish brown, was found on the surface, and thin and fragile ring of the same color was observed on the wall of the tube. Generation of gas and production of soluble pigments were not observed.

iii) Meat extract agar slant (at 28° C., for 2 days)

Colonies on the upper surface of the slant were translucent, slightly reddish pale yellow and wettish a little. Echinulate growth was observed on agar stroke. They had flat elevation and entire to undulate margin. On the other hand, colonies on the lower surface of the slant showed spreading growth, and the presence of the pale yellow verrucae were observed on surface. Generation of gas and production of soluble pigments were not observed.

iv) Meat extract gelatin stab culture (at room temperature, about 25° C., for 3 days)

Liquefaction was observed.

v) Litmus milk (at 28° C., for 2-11 days)

Acids formation was observed. Protein-coagulation and weak peptonization were observed. Upper layer was translucent reddish purple and lower layer was reddish cream-colored, forming thick coagulation body. Foams found in the above body suggested that PB-6042 had gas-producing ability. Thin gray pellicles were formed on the surface, and thin gray ring was also observed on the wall of the tube.

4. Physiological Characteristics (cultivated at 28° C.)
1) Oxidase test: negative
2) OF test: F type (Fermentation type). Facultative anaerobic property was observed.
3) Catalase test: slightly positive
4) Nitrate reduction: positive From the above data, and taking account of the fact that PB-6042 is Gram-negative, straight rod and shows active motility in a liquid medium by means of peritrichous flagella as mentioned above, it is clear that PB-6042 belongs to *Enterobacteriaceae*.

5) Denitrification: negative
6) Citrate utilization: positive (Simmons and Christiansen medium)
7) Malonate utilization: positive
8) Hydrolysis of esculin: positive
9) ONPG test: positive
10) Formation of H2S: negative
11) Forms indole: positive
12) Urease test: negative
13) Voges-Proskauer test: positive
14) Methyl red test: negative
15) Hydrolysis of arginine: positive
16) Decarboxylation of lysine: negative
17) Decarboxylation of ornithine: negative
18) Deoxyribonuclease (DNase) test: negative
19) Tween 80 esterase test: negative
20) Forms acid and gas from sugar:

i) Forms acid and gas from arabinose, xylose, glucose, mannitol, and melibiose;
ii) Forms acids but no gas from fructose, mannose, rhamnose, inosite, sucrose, and raffinose;
iii) Forms neither acid nor gas from adonitol, dulcitol, sorbitol, maltose, lactose, and trehalose.

The above-mentioned properties were utilized to identify PB-6042, on the basis of Bergey's Mannual of Systematic Bacterioloqy, vol.I, 1984, and it has been concluded that PB-6042 belongs to *Enterobacteriaceae* as suggested above. Further, PB-6042 can be assigned to *Enterobacter* genus among *Enterobacteriaceae*, in the light of the fact that PB-6042 is positive in Voges-Proskauer test, negative in methyl red test, deoxyribonuclease test, and Tween 80 esterase test, and can utilize citrate as a sole carbon source. Furthermore, PB-6042 is believed to be very closely related to *Enterobacter agglomerans* among *Enterobacter* genus, because it forms yellow colony and shows gelatin liquefaction and produces indole. PB-6042 produces acid and gas from sugars such as arabinose and glucose, which shows that PB-6042 belongs to gas-producing biogroup. In the light of the fact that PB-6042 is positive in Voges-Proskauer reaction and produces indole, PB-6042 can be assigned to biogroup G4.

each of antibiotics PB-6042A, B, C, and D is isolated by reversed phase HPLC. The antibiotics thus obtained are liposoluble and acidic compounds.

Antibacterial Activity of PB-6042s

PB-6042A, B, C, and D inhibit the growth of anaerobic bacteria, selectively. Table III summarizes the minimal inhibitory concentrations (MIC) of PB-6042s against various anaerobic bacteria. The MIC of PB-6042s of the present invention against anaerobic bacteria ranges from 1.56 to 12.5 $\mu$g/ml.

Table IV summarizes MIC of PB-6042A, B, C, and D against various aerobic bacteria.

One important aspect of the antibacterial activity of PB-6042s of the present invention relates to the fact that PB-6042s exhibit the antibacterial activity against both Gram-positive and Gram-negative anaerobic bacteria, while they exhibit weak activity against only a few Gram-positive aerobic bacteria. This feature is very useful and desirable in clinical applications.

PB-6042s were examined for the antibacterial mechanism up uptake-inhibition test using Bacillus sp. ATCC 21206, showing that inhibition of cytoplasmic membrane-formation is involved in the antibacterial activity.

TABLE 3

Antibacterial Activity of PB-6042A, B, C, and D against Anaerobic Bacteria

| Test Organism | MIC ($\mu$g/ml) | | | |
|---|---|---|---|---|
| | A | B | C | D |
| P. asaccharolyticus ATCC14963 | 12.5 | 6.25 | 3.13 | 6.25 |
| P. anaerobius B-38 | 3.13 | 3.13 | 0.78 | 1.56 |
| P. prevotii ATCC9321 | 12.5 | 6.25 | 3.13 | 6.25 |
| P. micros VPI5464-1 | 1.56 | 1.56 | 0.78 | 0.78 |
| S. constellatus ATCC27823 | 3.13 | 1.56 | 0.78 | 1.56 |
| E. lentum II-1 | 6.25 | 6.25 | 3.13 | 3.13 |
| E. limosum ATCC8486 | 6.25 | 3.13 | 1.56 | 3.13 |
| E. aerofaciens ATCC25986 | 12.5 | 6.25 | 3.13 | 6.25 |
| P. acens ATCC11827 | 3.13 | 3.13 | 0.78 | 1.56 |
| B. adolescentis JCM1250 | 12.5 | 6.25 | 0.78 | 6.25 |
| B. bifidum JCM1122 | 12.5 | 12.5 | 6.25 | 6.25 |
| B. longum ATCC15707 | 6.25 | 6.25 | 3.13 | 3.13 |
| L. plantarum JCM1100 | 12.5 | 12.5 | 6.25 | 6.25 |
| L. ruminis ATCC27780 | 6.25 | 3.13 | 1.56 | 3.13 |
| C. perfringens SAKAI | 12.5 | 6.25 | 3.13 | 3.13 |
| C. perfringens ATCC13124 | 12.5 | 6.25 | 3.13 | 3.13 |
| C. difficile ATCC17857 | 3.13 | 1.56 | 0.78 | 1.56 |
| V. parvula ATCC10790 | N.D. | N.D. | N.D. | >100 |
| B. fragilis GM7000 | 3.13 | 3.13 | 3.13 | 6.25 |
| B. fragilis ATCC25285 | 3.13 | 3.13 | 1.56 | 3.13 |
| B. thetaiotaomicron WAL3304 | 3.13 | 3.13 | 3.13 | 6.25 |
| B. vulgatus ATCC29327 | 3.13 | 3.13 | 3.13 | 12.5 |
| B. distasonis JU-11-1 | 3.13 | 3.13 | 3.13 | 12.5 |
| B. ovatus 2505 | 3.13 | 3.13 | 3.13 | 12.5 |
| B. melaninogenicus GAI0413 | 6.25 | 6.25 | 6.25 | 12.5 |
| F. varium ATCC8501 | >100 | >100 | >100 | >100 |
| F. necrophorum ATCC25286 | 6.25 | 12.5 | 12.5 | N.D. |
| F. nucleatum ATCC25586 | 6.25 | 12.5 | 12.5 | 25 |
| F. mortiferum ATCC9817 | 12.5 | 25 | 25 | >100 |

While G+C mole % of *Enterobacter agglomerans* strain ATCC 27155, which is the type strain, is 54.8% by HPLC, that of PB-6042 is 53.0% as described above, which value is within 53–58% range limited by Bergey's Manual, supra.

From the above data, it has been ascertained that PB-6042 belongs to *Enterobacter agglomerans*, and designated as *Enterobacter agglomerans* PB-6042.

Antibiotics PB-6042A, B, C, and D of the invention can be obtained from *Enterobacter agglomerans* PB-6042 by conventional procedures. In short, the culture of *Enterobacter agglomerans* PB-6042 is extracted with ethyl acetate, chromatographed over silica gel, and then

TABLE 4

Antibacterial Activity of PB-6042A, B, C, and D against Aerobic Bacteria

| Test Organism | MIC ($\mu$g/ml) | | | |
|---|---|---|---|---|
| | A | B | C | D |
| Gram-positive | | | | |
| S. aureus FDA JC-1 | 25 | 12.5 | >100 | >100 |
| S. aureus SR14(R) | >100 | 12.5 | >100 | 12.5 |
| S. pyogenes C-203 | 25 | 12.5 | 12.5 | 12.5 |
| S. pneumoniae TYPE 1 | 25 | 12.5 | 12.5 | 12.5 |

TABLE 4-continued

Antibacterial Activity of PB-6042A, B, C, and D against Aerobic Bacteria

| Test Organism | MIC (μg/ml) | | | |
|---|---|---|---|---|
| | A | B | C | D |
| Gram-negative | | | | |
| E. coli NIHJ JC-2 | >100 | >100 | >100 | >100 |
| K. pneumoniae SR1 | >100 | >100 | >100 | >100 |
| P. vulgaris CN-329 | >100 | >100 | >100 | >100 |
| P. aeruginosa A25619 | >100 | >100 | >100 | >100 |

The antibiotics of the present invention have been demonstrated to have an inhibitory action on platelet aggregation caused by collagen, and cytotoxic activity on tumor cells at concentrations of 20-40 μg/ml.

The following Example and Reference Examples are provided merely for the purpose of further illustrating the invention. The scope of the invention is not to be construed as merely consisting of the following Example.

EXAMPLE

Preparation of Antibiotics PB-6042A, B, C, and D

A. Fermentation

A cell suspension of PB-6042 (*Enterobacter agglomerans* strain) was used to inoculate 15 L of a medium (pH 7.0) containing 1.0% glucose, 0.5% Yeast extract, and 0.7% $CaCO_3$ in a 50-L Jar Fermentor. Then, the medium was incubated for 2 days at 32° C., while agitated at 450-600 rpm, aerated at 0.3-1.0 vvm, and kept at inner pressure of 0.35 $kg/cm^2$. *Clostridium difficile* ATCC 17857 was used for assay.

B. Isolation and Purification

To 32.5 L of the cultured broth, prepared as described in Section A, was added 6 kg of NaCl and 10 L of ethyl acetate. The mixture was adjusted to pH 4.0 with HCl, stirred for 30 minutes, and centrifuged by Westfaria Separator TA-1. The ethyl acetate phase was separated, washed successively with 2% $NaHCO_3$ (pH 8.6) and water, and the solvent was evaporated. Twenty four grams of the resultant oil residue was dissolved in 50 ml of chloroform/methanol (7:3), and chromatographed over silica gel (Silica Gel 60, 3.6×40 cm, 407 ml), using chloroform/methanol (9:1) as an eluent. Fractions eluted were assayed using Clostridium difficile-plate assay. Positive fractions were combined and the solvent was evaporated. The resultant residue was mixed with petroleum ether to give the product as a precipitate. The product was dissolved again in ethyl acetate/methanol (8:2), and chromatographed over silica gel (Merck Silicagel 60, 3.6×40 cm, 407 ml), using ethyl acetate as an eluent. Fractions containing the product were combined and the solvent was evaporated. Subsequently, the resultant residue was taken up with petroleum ether to give 1.6 g of the product as a precipitate.

The product was dissolved in 20 ml of chloroform/methanol (9:1), and chromatographed over silica gel (Merck Silicagel 60, 3.6×40 cm, 407 ml), using chloroform and then chloroform/methanol (9:1) as eluents. Fractions containing the product were combined and the solvent was evaporated. The resultant residue was mixed with petroleum ether to give 1.03 g of the product as a precipitate. The resultant product was subject to preparative HPLC (Nucleosil 10 $C_{18}$ column (2.0 x 25 cm)), by injecting on of the product in methanol, eluting with 48% acetonitrile/·50mM PBS pH 7.5, 50mM $Na_2SO_4$, and monitoring at 260 nm, and 900 ml, 900 ml, 1150 ml, and 740 ml of fractions containing PB-6042A, PB-6042B, PB-6042C, and PB-6042D respectively, were collected. These fractions were each evaporated, extracted with ethyl acetate, washed with water, dried over sodium sulfate, and the solvents were evaporated. The residues were mixed with petroleum ether to yield 115 mg, 92 mg, 74 mg, and 24 mg of PB-6042A, B, C, and D respectively, in the form of sodium salts as powders.

REFERENCE EXAMPLE 1

Reduction of PB-6042A

Fifty milligrams of sodium salt of PB-6042A was dissolved in 8 ml of methanol, and subject to hydrogenation in the presence of 35 mg of $PtO_2$ under atmosphere of hydrogen for two hours. After filtration of the catalyst, the filtrate was concentrated and subjected to preparative thin layer chromatography (6 silica gel plates (250μ), ethyl acetate/methanol (9:1)). The gel at the position of Rf value of 0.24 was extracted with chloroform, and the extract was evaporated. The residue was then partitioned between ethyl acetate and a dilute $NaHCO_3$ solution, and the ethyl acetate phase was washed with water, dried over sodium sulfate, and evaporated. The residue was precipitated by the addition of petroleum ether to yield 22 mg of the desired product.

REFERENCE EXAMPLE 2

Methylation of reduced PB-6042A

Sixty milligrams of sodium salt of PB-6042A was dissolved in 8 ml of methanol, and hydrogenated with 30 mg of $PtO_2$ under atmosphere of hydrogen for 35 minutes. The reaction mixture was treated according to the procedure as described in Reference Example 1, and the gel was extracted with chloroform/methanol (1:1), and the extract was evaporated. The residue was then partitioned between ethyl acetate and water (pH 3), and the ethyl acetate phase was washed with water, dried over sodium sulfate, and evaporated. After addition of $CH_2N_2$, the mixture was allowed to stand on ice for 10 minutes, and evaporated to yield the methylated product, which was subject to HPLC analysis under the following conditions:

Column: Nucleocil 5 $C_{18}$ (No. 3), 2×25 cm,
Eluent: 60% acetonitrile/20mM $Na_2HSO_4$, pH 7.0,
Flow rate: 15.75 ml/min.,
Chart speed: 0.5 cm/min.,
OD: 254 nm,
Retention time: 22.3 min.,
Retention volume: 350 ml.

Pooled fractions (320 ml) were evaporated, and the resultant residue was extracted with 80 ml of ethyl acetate, washed with water, dried over sodium sulfate, and evaporated to yield 22 mg of methylated product.

What we claim is:

1. A compound of the formula (I):

wherein R is
(CH$_2$)$_8$CH$_3$,
(CH$_2$)$_3$CH(cis)CH(CH$_2$)$_5$CH$_3$,
(CH$_2$)$_{10}$CH$_3$, or
(CH$_2$)$_4$CH(cis)CH(CH$_2$)$_6$CH$_3$.
or salt thereof.

2. A process for producing the compounds of claim 1, which comprises cultivating a microorganism of belonging to the Enterobacter genus in a suitable culture medium and isolating said compounds.

3. The process according to claim 2, wherein said microorganism is *Enterobacter agglomerance*.

4. The process according to claim 3, wherein said microorganism is *Enterobacter agglomerance PB*-6042.